(12) United States Patent
Russo

(10) Patent No.: US 6,296,164 B1
(45) Date of Patent: Oct. 2, 2001

(54) MEDICAL DEVICE HOLDER

(75) Inventor: Ronald D. Russo, Barrington, RI (US)

(73) Assignee: Dale Medical Products, Inc., Plainville, MA (US)

( * ) Notice: Subject to any disclaimer, the term of this patent is extended or adjusted under 35 U.S.C. 154(b) by 0 days.

(21) Appl. No.: 09/352,572

(22) Filed: Jul. 13, 1999

(51) Int. Cl.[7] .................................................. A45C 13/30
(52) U.S. Cl. ......................... 224/602; 224/581; 224/603; 224/605; 224/660; 224/901.4; 224/901.6; 224/901.8
(58) Field of Search ................................ 224/148.1, 148.2, 224/148.5, 148.6, 578, 581, 582, 583, 602, 603, 604, 605, 660, 231, 235, 236, 250, 901.2, 901.4, 901.6, 901.8

(56) References Cited

U.S. PATENT DOCUMENTS

| | | |
|---|---|---|
| D. 393,310 | 4/1998 | Russo . |
| 3,022,786 | 2/1962 | Nalon . |
| 4,079,767 * | 3/1978 | Howard .............................. 224/235 X |
| 4,096,853 | 6/1978 | Weigand . |
| 4,191,180 | 3/1980 | Colley et al. . |
| 4,423,834 * | 1/1984 | Rush ................. 224/236 X |
| 4,578,062 | 3/1986 | Schneider . |
| 4,582,508 | 4/1986 | Pavelka . |
| 4,596,560 | 6/1986 | Simpson . |
| 4,610,245 | 9/1986 | Biearman . |
| 4,666,432 | 5/1987 | McNeish et al. . |
| 4,799,923 | 1/1989 | Campbell . |
| 4,811,768 | 3/1989 | Williams . |
| 4,897,082 | 1/1990 | Erskine . |
| 4,966,320 * | 10/1990 | DeSantis et al. .............. 224/901.4 X |
| 5,048,512 | 9/1991 | Turner et al. . |
| 5,116,324 | 5/1992 | Brierley et al. . |
| 5,135,519 | 8/1992 | Helmer . |
| 5,147,320 | 9/1992 | Reynolds et al. . |
| 5,240,156 | 8/1993 | Sicotte et al. . |
| 5,304,145 | 4/1994 | Blair . |
| 5,336,195 | 8/1994 | Daneshvar . |
| 5,403,285 | 4/1995 | Roberts . |
| 5,496,282 | 3/1996 | Militzer et al. . |
| 5,643,233 | 7/1997 | Turner . |
| 5,938,089 * | 8/1999 | Abreu-Marston ................. 224/148.5 |
| 5,964,386 * | 10/1999 | Cote .................................... 224/250 |

FOREIGN PATENT DOCUMENTS 0 661 027    7/1995   (EP) .

\* cited by examiner

Primary Examiner—Stephen K. Cronin
(74) Attorney, Agent, or Firm—Wolf, Greenfield & Sacks, P.C.

(57) ABSTRACT

An apparatus is provided for securing a medical device on a patient's body. According to one preferred embodiment, a medical device holder is provided that includes a strap for attachment to a patient, a pouch attached to the strap, the pouch including a front layer and a back layer that forms a pocket for receiving the medical device, and a first fastener fixedly attached to an inner surface of the front layer to attach the front layer to the back layer to secure the medical device in the pouch.

22 Claims, 5 Drawing Sheets

MEDICAL DEVICE HOLDER

BACKGROUND OF THE INVENTION

A gastronomy feeding tube is frequently used when a patient is unable to ingest food or drink orally. The tube is connected directly to the patient's stomach or intestinal tract so that the patient can receive nourishment directly via the tube. When the feeding tube is not in use, it remains attached to the patient to avoid re-connection each time the patient is fed.

Typically, the tube either hangs freely from the patient or is attached by medical tape or some other adhesive holder to the skin of the patient. Thus, the tube is exposed and susceptible to patient or care giver pull out which could cause injury to the patient. Also, adhesive holders used to hold the tube in place are uncomfortable and irritate the patient's skin.

Another medical device which is attached to a patient is a wound drainage bulb which is attached to a wound via a tube. The bulb is used as a suction reservoir to drain fluid from post-operative wounds.

Like gastronomy feeding tubes, the drainage bulb is also typically either left hanging from the patient or taped to the patient with uncomfortable adhesive backed holders or medical tape. The discomfort and awkwardness of the exposed wound drainage bulb also often leads to patient or accidental pullout.

SUMMARY OF THE INVENTION

An apparatus is provided for securing a medical device on a patient's body.

According to one preferred embodiment, a medical device holder is provided that includes a strap for attachment to a patient, a pouch attached to the strap, the pouch including a front layer and a back layer that forms a pocket for receiving the medical device, and a first fastener fixedly attached to an inner surface of the front layer to attach the front layer to the back layer to secure the medical device in the pouch.

According to another preferred embodiment, a medical device holder is provided that includes a strap for attachment to a patient, a first pouch attached to the strap, the pouch including a front layer and a back layer that forms a pocket for receiving a first medical device, and a second pouch attached to the strap, the second pouch including a front layer and a back layer that forms a pocket for receiving a second medical device.

DETAILED DESCRIPTION

Figure 1:
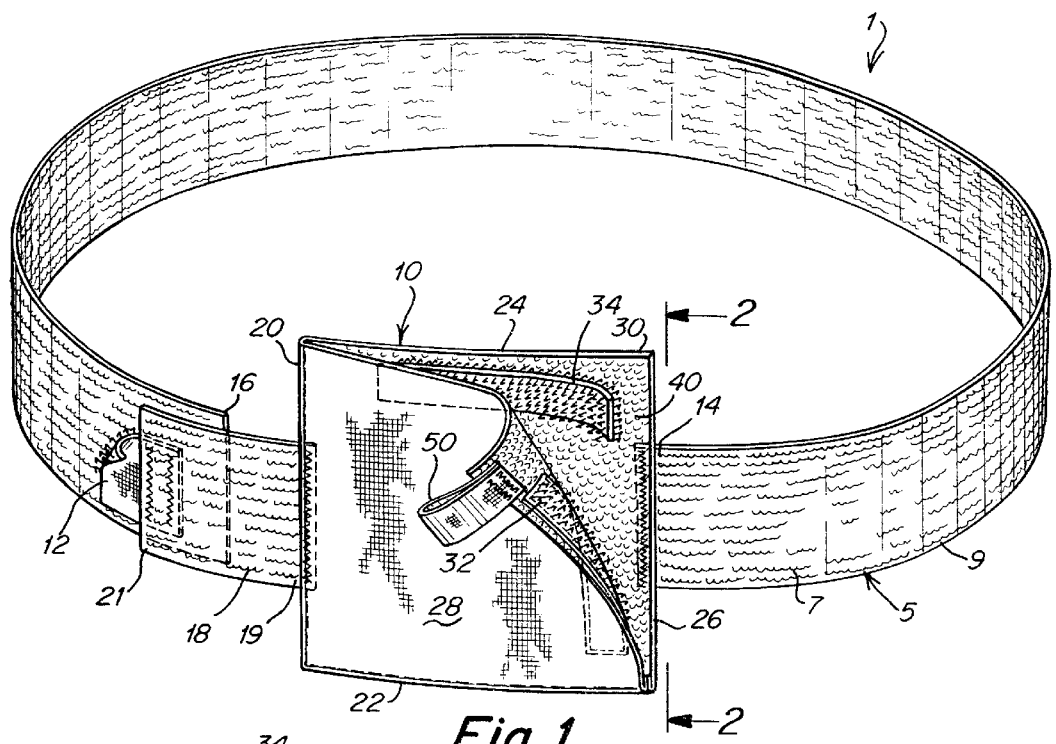
FIG. 1 is a perspective view of one embodiment of a medical device holder.

FIGS. 1–5 show a preferred embodiment of a medical device holder according to the present invention. The holder 1 includes a strap 5 and a pouch 10 fixedly attached to the strap 5. The strap is used to support the pouch on a patient's body so that the patient can secure various medical devices inside of pouch 10. For example, in the foregoing preferred embodiments the holder is used to secure wound drainage bulbs (42 of FIG. 3) or gastronomy feeding tubes (52 of FIG. 4). The holder can also be used to secure other various types of medical devices in which it is desirable to have the device remain stable and unexposed. Such medical devices include, for example, jejunostomy tubes, PEG tubes, balloon replacement G-tubes, Foley catheters used as G-tubes, etc.

Figure 8:
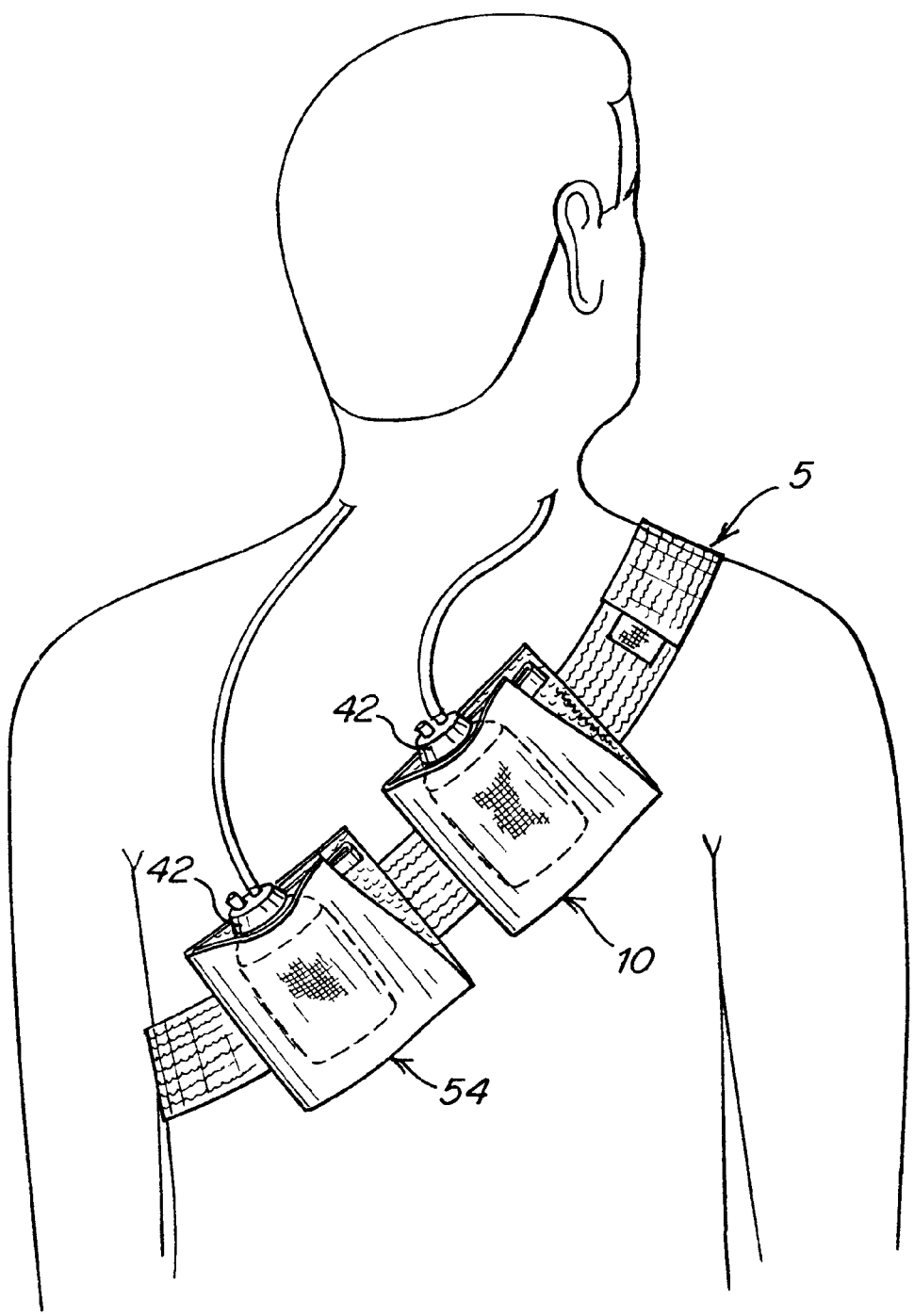
FIG. 8 shows the medical device holder of FIG. 7 in use.

The strap 5 is shown attached as a belt around a patient's waist, however, the strap can be attached to other areas of the patient's body as needed (see FIG. 8). The strap is made of stretchable material and can be adjustable to various sizes to accommodate different sized patients and different parts of the patient's body. The strap 5 includes a first section 9 having a first end 14 attached to the pouch. In the foregoing preferred embodiment the first end 14 of the strap is attached to the pouch via stitching.

The strap also includes a second section 18 having a first end 19 attached to a side of the pouch opposite the side of the pouch the first end 14 of the first section 9 is attached. The first end 19 is also attached via stitching to the pouch 10 in this embodiment. The second end 21 of the strap includes a hook fastener 12 attached thereto (also by stitching). The hook fastener 12 can be attached anywhere along the surface of the first section 9 of the strap 5 which includes a loop fastener material 7 along its entire surface. Accordingly, using fastener 12 the strap can be adjusted to different size patients and different areas of a patient's body.

Pouch 10 is made from a rectangular sheet of material which is folded at a first side 20 of the pouch, and sewn together at a second side 22 of the pouch, to form a pocket including a front layer 28 and a rear layer 30 of the pouch. As shown in FIG. 1, the pouch can be opened at a third side 24 and a fourth side 26 opposite the folded side 20. Any appropriate material can be used to form the pouch, however, preferably a soft, cloth material is used that will not irritate the patient's skin. Further, the pouch can be manufactured in various sizes, for example, 6"×6" is appropriate for larger medical devices such as drainage bulbs. It should also be noted that although in the forgoing embodiment the pouch is formed as a rectangle or square shape, various other shapes may form the pouch, such as circular, oval, etc.

Figures 2, 2A:
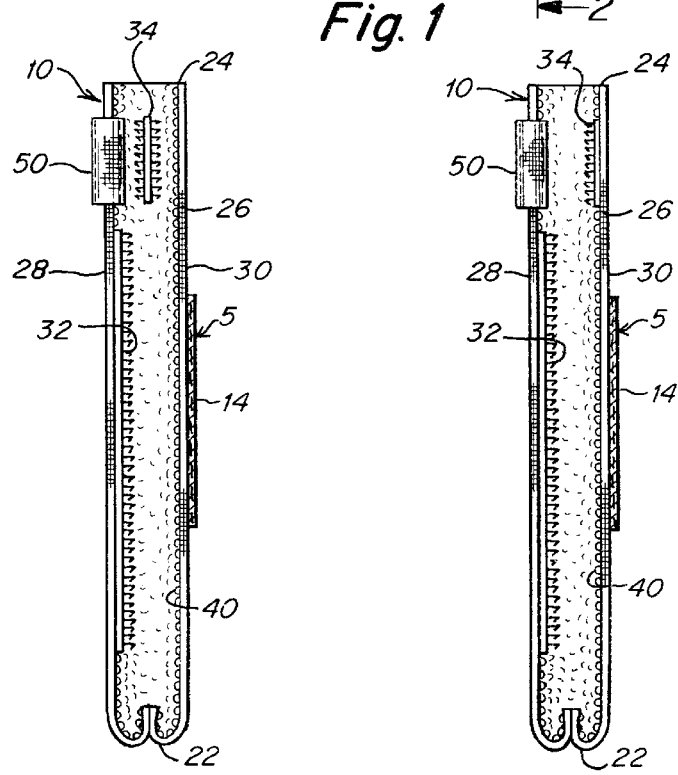
FIG. 2 is a right side cross-sectional view of the holder of FIG. 1, taken along line 2—2 of FIG. 1.
FIG. 2A is a right side cross-sectional view similar to FIG. 2, of an alternative embodiment of a medical device holder in which the top fastener is stitched to the inside panel.

The pouch also includes a first hook fastener 32 sewn to the inner edge of front layer 28, and a second hook fastener 34 which includes hooks on both sides and is free floating, i.e., attachable anywhere along the inner surfaces of the front or back layers 28 and 30 (see FIG. 2). Alternatively, the second hook fastener 34 can be sewn to the top of the rear layer (see FIG. 2A), or the top of the front layer. The inner surfaces of both the front layer 28 and the rear layer 30 of the pouch 10 include a loop material 40 along an entire surface thereof to enable fasteners 32 and 34 to be attached anywhere along the inner surfaces of the rear and front layers, respectively.

Figure 3:
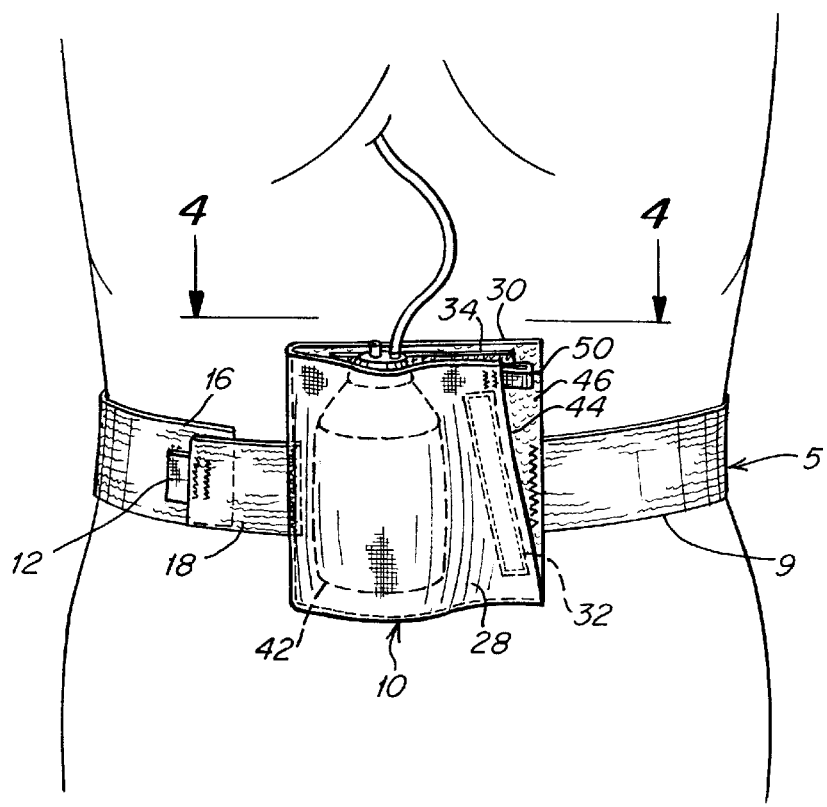
FIG. 3 is a perspective view of the medical device holder of FIG. 3, in use holding a drainage bulb.
Figure 4:
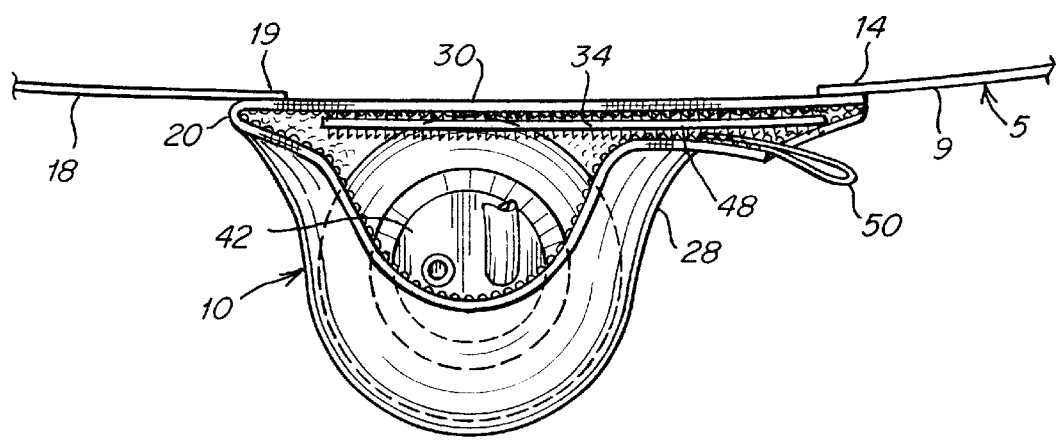
FIG. 4 is an enlarged top plan view of the pouch area of FIG. 3, as seen along line 4—4 of FIG. 3.

To hold a medical device in the pouch 10 (after attaching the strap 5 to the patient), front layer 28 is pulled away from rear layer 30 and the apparatus is placed inside the pouch. The device is secured in place by securing hook fastener 32 on the front panel to a surface of the rear layer 30 and securing the top of the front layer to the rear layer 30 via two-sided hook fastener 34. FIGS. 3 and 4 show a wound drainage bulb 42 secured in the pouch. A tab 50 is provided to easily lift the front layer away from the rear layer and release the fasteners 32 and 34.

As shown in FIG. 4, the front layer 28 conforms to the shape of the device to keep the device immobile. Sewing the hook fastener 32 on the front layer 30 enables irregularly shaped, non-flat devices (like the drainage bulb) to be held securely in place since the hook fastener 32 can be attached anywhere along the rear layer 30. For example, as shown in FIGS. 3 and 4, fastener 32 is attached directly adjacent the drainage bulb 42 and prevents little if any lateral movement or shifting of the bulb in the pouch, thereby preventing aggravation of the wound area. Further, if the hook fastener 32 were attached to the inner edge 46 of the rear layer 30, the edge 44 of the front layer may not reach the edge 46 for attachment thereto (see FIG. 3) due to the shape of the bulb 42.

The use of a free floating hook fastener 34 also enables the front layer to be adhered to the rear layer if the edges of the top and rear layer do not mate perfectly to one another. As seen in FIG. 4, due to the volume occupied by the drainage bulb 42, the loop surface of the front layer 28 attaches to the fastener 34 only in a relatively small section 48 of the fastener 34, which is attached to the rear layer 30 of the pouch.

Figure 5:
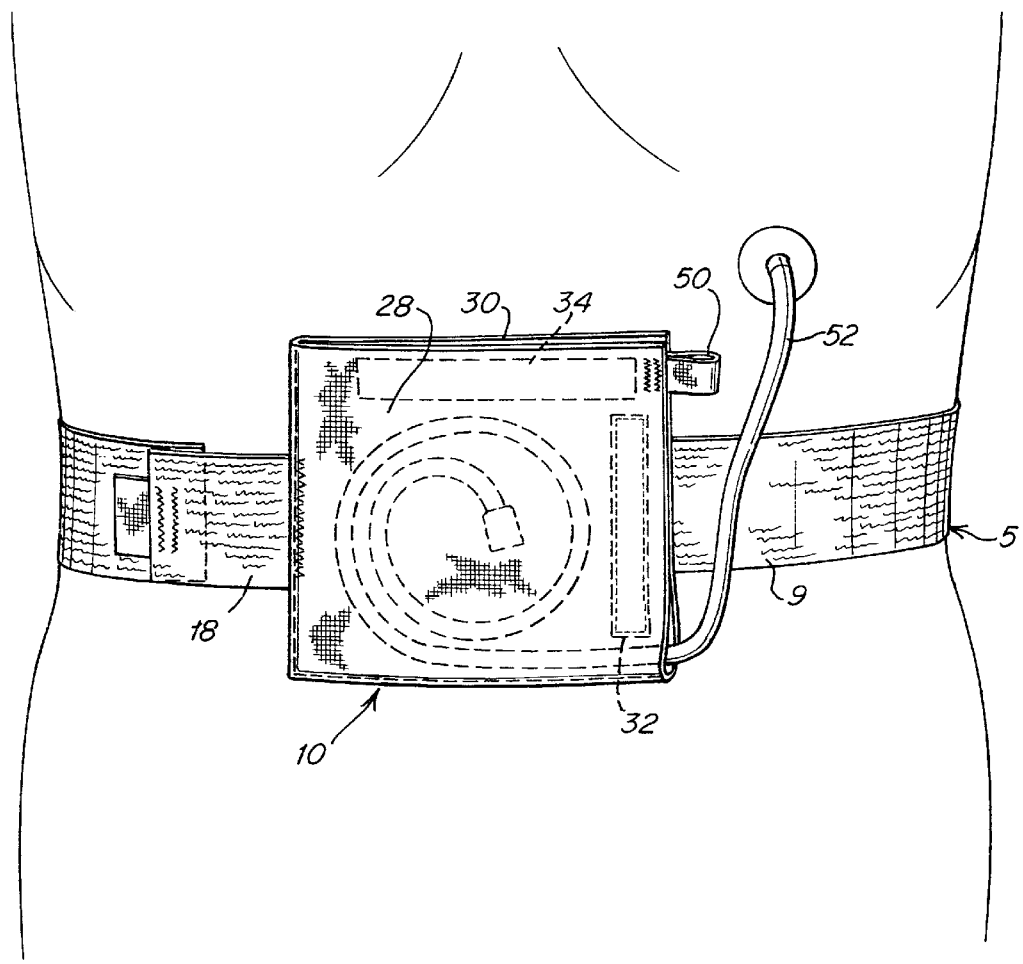
FIG. 5 is a perspective view of the medical device holder of FIG. 1, in use holding a feeding tube.

FIG. 5 shows an alternative use of the holder 1 of FIGS. 1–4 in which a feeding tube 52 is held in the pouch 10. In FIG. 5, the feeding tube is not in use and is stored securely in the pouch 10 to prevent accidental dislodgement, and discourage patient pull out. Although not shown, the pouch can include a slit in the rear layer 30 to receive the tube 52.

Figure 6:
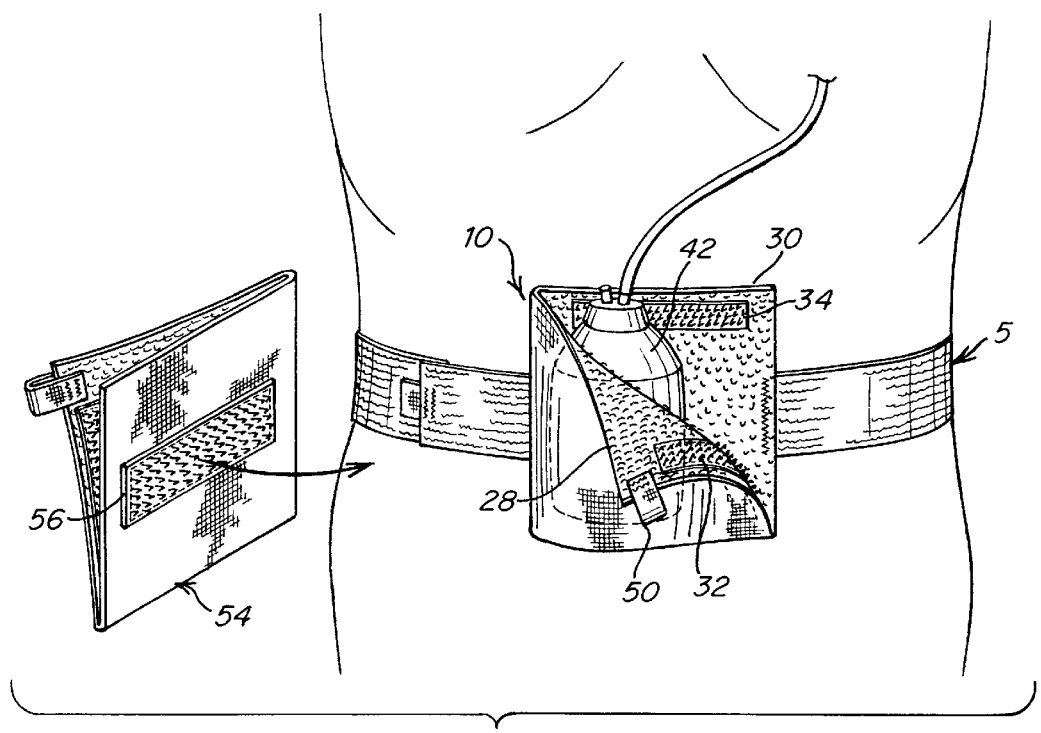
FIG. 6 is an exploded perspective view of an alternative embodiment of a medical device holder which utilizes two or more pouches.
Figure 7:
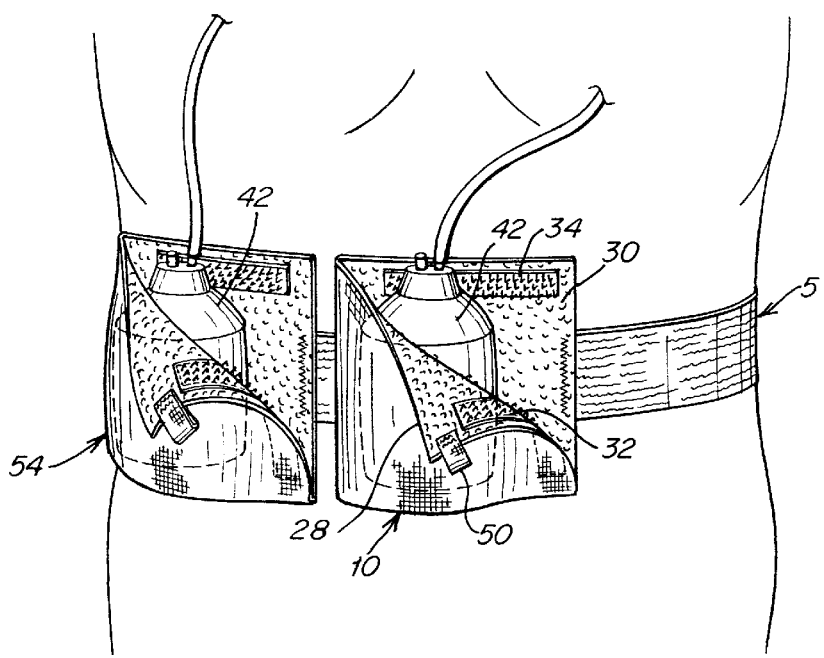
FIG. 7 shows the medical device holder of FIG. 6 with the add-on pouch attached to the belt.

FIGS. 6–8 show an alternative embodiment in which pouches 54 can be added on to strap 5 to hold additional drainage bulbs and/or other medical devices. The add-on pouch 54 includes a hook fastener 56 attached to the rear layer of the pouch 54 which can attach anywhere along the surface of the strap 5, which, as stated above, includes a loop fastener material along its entire surface. Accordingly, as shown in FIGS. 7 and 8, the add-on pouch can be used to hold an additional wound drainage bulb.

Having thus described certain embodiments of the present invention, various alterations, modifications, and improvements will readily occur to those skilled in the art. Such alterations, modifications, and improvements are intended to be within the spirit and scope of the invention. Accordingly, the foregoing description is by way of example only, and not intended to be limiting.

What is claimed is:

1. A medical device holder comprising:
   a strap for attachment to a patient;
   a pouch attached to the strap, the pouch including a front layer and a back layer, the front layer being attached or attachable to the back layer along substantially an entire periphery thereof so as to form a pocket for receiving the medical device; and
   a first fastener fixedly attached to an inner surface of the front layer to removably attach the front layer to the back layer to secure the medical device in the pouch.

2. The medical device holder of claim 1, further comprising a second fastener to attach the front layer to the back layer.

3. The medical device holder of claim 1, wherein the first fastener is a hook fastener and an inner surface of the back layer includes loop material thereon to engage the first fastener.

4. The medical device holder of claim 1, wherein the front layer is permanently attached to the rear layer along a portion of a periphery of the pouch.

5. The medical device holder of claim 1, wherein the pouch is rectangular in shape.

6. The medical device holder of claim 1, further comprising a second pouch attached to the strap.

7. The medical device holder of claim 6, wherein the second pouch is removably attached to the strap.

8. The medical device holder of claim 7, wherein the first pouch is permanently attached to the strap.

9. A medical device holder comprising:
   a strap for attachment to a patient;
   a pouch attached to the strap, the pouch including a front layer and a back layer that forms a pocket for receiving the medical device; and
   a first fastener fixedly attached to an inner surface of the front layer to removably attach the front layer to the back layer to secure the medical device in the pouch, wherein the first fastener can be attached to any location on an inner surface of the back layer.

10. A medical device holder comprising:
    a strap for attachment to a patient;
    a pouch attached to the strap, the pouch including a front layer and a back layer that forms a pocket for receiving the medical device; and
    a first fastener fixedly attached to an inner surface of the front layer to removably attach the front layer to the back layer to secure the medical device in the pouch, wherein the pouch includes first and second sides that are permanently attached and third and fourth sides that are removably attached.

11. The medical device holder of claim 10, wherein the first fastener is a hook fastener and an inner surface of the back layer includes loop material thereon to engage the first fastener.

12. The medical device holder of claim 10, wherein the first fastener removably attaches the third side to the back layer.

13. The medical device holder of claim 12, further comprising a second fastener to removably attach the fourth side to the back layer.

14. The medical device holder of claim 13, wherein the second fastener is a free-floating hook fastener.

15. The medical device holder of claim 10, further comprising a second pouch attached to the strap.

16. The medical device holder of claim 15, wherein the second pouch is removably attached to the strap.

17. The medical device holder of claim 16, wherein the first pouch is permanently attached to the strap.

18. A medical device holder comprising:
    a strap for attachment to a patient;
    a first pouch attached to the strap, the pouch including a front layer and a back layer that forms a pocket for receiving a first medical device; and
    a second pouch attached to the strap, the second pouch including a front layer and a back layer that forms a pocket for receiving a second medical device, wherein the first and second pouches are externally located with respect to one another.

19. The medical device holder of claim 18, wherein the second pouch is removably attached to the strap.

20. The medical device holder of claim 19, wherein the first pouch is permanently attached to the strap.

21. The medical device holder of claim 18, wherein the front layer of each of the first and second pouches is attached or attachable to the back layer along substantially an entire periphery thereof so as to form a pocket for receiving the first and second medical devices.

22. The medical device holder of claim 21, wherein each of the first and second pouches includes first and second sides that are permanently attached and third and fourth sides that are removably attached.

* * * * *